(12) United States Patent
Elliott

(10) Patent No.: US 6,949,564 B2
(45) Date of Patent: Sep. 27, 2005

(54) NPY-5 ANTAGONISTS

(75) Inventor: Richard L. Elliott, East Lyme, CT (US)

(73) Assignee: Pfizer Inc., New York, NY (US)

( * ) Notice: Subject to any disclaimer, the term of this patent is extended or adjusted under 35 U.S.C. 154(b) by 8 days.

(21) Appl. No.: 10/724,962

(22) Filed: Dec. 1, 2003

(65) Prior Publication Data

US 2004/0122046 A1 Jun. 24, 2004

Related U.S. Application Data

(60) Provisional application No. 60/434,373, filed on Dec. 18, 2002.

(51) Int. Cl.$^7$ .................. A61K 31/44; C07D 413/00
(52) U.S. Cl. .................. 514/303; 514/341; 514/397; 546/118; 546/271.4; 548/312.1
(58) Field of Search ...................... 548/312.1

(56) References Cited

U.S. PATENT DOCUMENTS

| 5,576,337 A | 11/1996 | Bruns, Jr. et al. ........... 514/324 |
| 2004/0067999 A1 | 4/2004 | Block et al. ................ 514/415 |

FOREIGN PATENT DOCUMENTS

| EP | 0759441 | 2/1997 | ........... C07K/14/47 |
| WO | WO 9901128 | 1/1999 | ......... A61K/31/415 |

OTHER PUBLICATIONS

Harfenist et al. et al, Selective inhibitors of Monoamine Oxidase. 3. Structure—Activity Relationship of Tricyclics Bearing Imidazoline, Oxadiazoe, or Tetrazole Groups. Journal of Medicinal Chemistry 1996, 39(9), 1857–63.*
A. Balasubramaniam, Am. J. of Surgery, 183, pp. 430–434, 2002.
Flood and Mortey Peptides, 10, pp. 963–966, 1989.
Leibowitz and Alexander, Peptides, 12, pp. 1251–1260, 1991.
Stanley et al., Peptides, 13, pp. 581–587, 1992.
McCauley and Westfal, J. Pharmacol, Exp. Ther. 261, pp. 863–868, 1992.
Grundemar et al., Br. J. Pharmacol, 105, pp. 45–50, 1992.
Grundemar and Hakanson, TIPS, May 1994, vol. 15, pp. 153–159.
Wahlestedt et al., Regul. Peptides, 13, pp. 307–318, 1986.
Redrobe et al., Life Sciences, 71, pp. 2921–2937, 2002.
Chemical Abstracts, vol. 124, No. 11, 1996, Columbus, Ohio, U.S.; abstract No. 146013g, Berghot, Moged Ahmed et al., "Facile Synthesis of Nevl Carbazoles Through Heterocyclization Reactions and Their Antimicrobial Activity", XP002277868.
Abstract and Rev. Roum. Chim., vol. 40, No. 4, 1995, pp 377–386, and Database Caplux "online" Chemical Abstracts Service, Columbus, Ohio, U.S., Database Accession No. 124:146013, XP002277869, Compound with RN 173463–46–2.
Hammond M. et al., Bioorganic & Medicinal Chemistry Letters, 2003, vol. 13, No. 8, pp 1989–1992, "Structure–Activity Relationships in a Series of NPY Y5 Antagonists: 3–Amido–ethylcarbazoles, Core–Modified Analogues and Amide Isosteres".

* cited by examiner

Primary Examiner—Kamal A. Saeed
(74) Attorney, Agent, or Firm—Peter C. Richardson; Gregg C. Benson; Arlene K. Musser

(57) ABSTRACT

The present invention provides NPY-5 receptor antagonists having a Formula (IA)

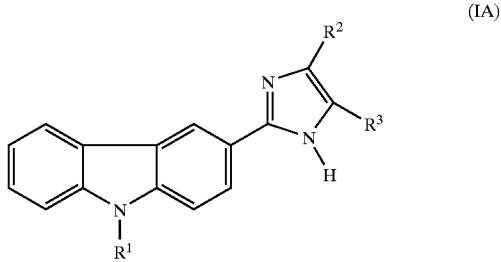

(IA)

Methods and pharmaceutical compositions useful for treating diseases, conditions and/or disorders modulated by the above NPY-5 receptor antagonists are also provided.

6 Claims, No Drawings

NPY-5 ANTAGONISTS

This application claims the benefit of U.S. Provisional Application No. 60/434,373 filed on Dec. 18, 2002 and incorporated herein by reference in its entirety.

FIELD OF INVENTION

The present invention relates to carbazole NPY-5 antagonists and their use in treating diseases, conditions and/or disorders modulated by NPY-5 receptor antagonists.

BACKGROUND

Neuropeptide Y (NPY), a 36 amino acid peptide neurotransmitter, is a member of the pancreatic polypeptide class of neurotransmitters/neurohormones. NPY is widely distributed throughout the central nervous system and is one of the most conserved peptide in evolution, suggesting an important role in the regulation of basic physiological functions. Investigations to date have implicated NPY in the pathophysiology of a number of diseases including feeding disorders, seizures, anxiety, diabetes, hypertension, cancer (e.g., breast and pancreatic cancer), nasal congestion, sexual dysfunctions, congestive heart failure, and intestinal dysfunctions. At least 6 NPY receptor subclasses have been identified and cloned to date, with two of these subclasses, NPY-1 and NPY-5, thought to be the most important receptor subtypes modulating food intake and energy expenditure. See, Balasubramaniam, A., "Clinical potentials of neuropeptide Y family of hormones," *Am. J. of Surgery*, 183, 430–434 (2002) for a review.

Various animal studies have shown that activation of neuropeptide Y receptors is related to stimulation of consummatory behavior, Flood and Morley *Peptides*, 10, 963–966 (1989), Leibowitz and Alexander, *Peptides*, 12,1251–1260 (1991), and Stanley et al. *Peptides*, 13, 581–587 (1992), and to vasoconstriction, Wahlestedt et al. *Regul. Peptides*, 13, 307–318 (1986), McCauley and Wesffall *J. Pharmacol. Exp. Ther.* 261, 863–868 (1992), and Grundemar et al. *Br. J. Pharmacol.* 105, 45–50 (1992).

Further, Grundemar and Hakanson *TIPS*, May 1994 [Vol. 15], 153–159, state that in animals, NPY is a powerful stimulus of food intake and inducer of vasoconstriction leading to hypertension. They also point out that low levels of NPY are associated with loss of appetite. The reports clearly indicate that compounds that inhibit the activity of this protein will reduce hypertension and appetite in animals.

Hence, agents capable of blocking NPY binding at these receptor subtype(s) should have utility in a number of feeding disorders including obesity, anorexia nervosa, bulimia nervosa; obesity-related disorders including but not limited to insulin resistance, diabetes, hyperlipidemia, and hypertension, as well other indications for treatment where blockade of NPY activity is beneficial.

In addition, both pre-clinical and clinical evidence have suggested that NPY, together with its receptors, may have a direct implication in several psychiatric disorders, including depression and related illnesses. NPY-like immunoreactivity and NPY receptors are expressed through out the brain, with varying concentrations being found throughout the limbic system. Such brain structures have been repeatedly implicated in the modulation of emotional processing, as well as in the pathogenesis of depressive disorders. For a review, see, Redrobe, J. P., et al., "Neuropeptide Y (NPY) and Depression: From Animal Studies to the Human Condition," *Life Sciences*, 71, 2921–2937 (2002).

EP0759441 and U.S. Pat. No. 5,576,337 report physiological disorders related to any excess of NPY.

WO 99/01128 discloses certain NPY-5 receptor mediators useful for treating feeding disorders such as obesity and bulima as well as certain cardiovascular diseases such as essential hypertension.

Although NPY-5 receptor antagonists are known, there still exists a need for additional antagonists that may be useful in the treatment of diseases modulated by NPY-5 receptor antagonists especially in light of the important role NPY receptors play in the regulation of the basic physiological functions discussed above.

SUMMARY

The present invention provides a compound of Formula (IA)

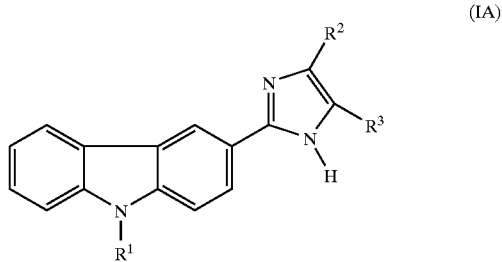

(IA)

wherein
R$^1$ is hydrogen or (C$_1$–C$_4$)alkyl;
R$^2$ is hydrogen, (C$_1$–C$_4$)alkyl, aryl, or a 5–6 membered heteroaryl containing one to three heteroatoms selected from oxygen, nitrogen, or sulfur; and
R$^3$ is hydrogen, (C$_1$–C$_4$)alkyl, or halo-substituted (C$_1$–C$_4$) alkyl;
or R$^2$ and R$^3$ taken together form an optionally substituted aromatic six-membered heterocyclic ring, where said heterocyclic ring contains 1 to 2 nitrogen ring atoms, or an optionally substituted aromatic six-membered carbocyclic ring (preferably, the aromatic six-membered carbocyclic ring is mono-substituted);
a pharmaceutically acceptable salt thereof, a prodrug of the compound or the salt, or a solvate or hydrate of the compound, the salt or the prodrug.

Preferred compounds of Formula (IA) include 9-ethyl-3-(5-methyl-4-phenyl-1H-imidazol-2-yl)-9H-carbazole; 9-ethyl-3-(4-phenyl-5-trifluoromethyl-1H-imidazol-2-yl)-9H-carbazole; 9-ethyl-3-(5-methyl-4-pyridin-2-yl-1H-imidazol-2-yl)-9H-carbazole; 3-(4,5-dimethyl-1H-imidazol-2-yl)-9-ethyl-9H-carbazole; 9-ethyl-3-(1H-imidazo[4,5-c]pyridin-2-yl)-9H-carbazole; 3-(1H-benzoimidazol-2-yl)-9-ethyl-9H-carbazole; 9-ethyl-3-(3H-imidazo[4,5-b]pyridin-2-yl)-9H-carbazole; 9-ethyl-3-(7H-purin-8-yl)-9H-carbazole; and 2-(9-ethyl-9H-carbazol-3-yl)-1H-benzoimidazole-5-carboxylic acid; a pharmaceutically acceptable salt thereof or a solvate or hydrate of the compound or the salt.

Those skilled in the art will recognize that the imidazole ring may exist in tautomeric forms; therefore, the tautomers form a part of the present invention.

In another embodiment of the present invention, a pharmaceutical composition is provided that comprises (1) a compound of the present invention and (2) a pharmaceutically acceptable excipient, diluent, or carrier. Preferably, the composition comprises a therapeutically effective amount of a compound of the present invention. The composition may also contain at least one additional pharmaceutical agent (described herein).

In yet another embodiment of the present invention, a method for treating a disease, condition or disorder modulated by a NPY-5 receptor antagonist in animals that includes the step of administering to an animal in need of such treatment a therapeutically effective amount of a compound of the present invention (or a pharmaceutical composition thereof). Diseases, conditions, and/or disorders modulated by NPY-5 receptor antagonists include obesity, feeding disorders (e.g., anorexia nervosa and bulimia nervosa), seizures, anxiety, diabetes, hypertension, hyperlipidemia, cancer (e.g., breast and pancreatic cancer), nasal congestion, sexual dysfunctions, congestive heart failure, intestinal dysfunctions, and psychiatric disorders (e.g., depression).

Compounds of the present invention may be administered in combination with other pharmaceutical agents (described herein). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

Definitions

As used herein, the term "alkyl" refers to a hydrocarbon radical of the general formula $C_nH_{2n+1}$. The alkane radical may be straight or branched. For example, the term "$(C_1-C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. "Halo-substituted alkyl" refers to an alkyl group substituted with one or more halogen atoms (e.g., fluoromethyl, difluoromethyl, trifluoromethyl, perfluoroethyl, and the like).

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) selected from sulfur, oxygen and/or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When indicated as being "optionally substituted", the partially saturated or fully saturated heterocycle group may be unsubstiuted or substituted with one of more substituents (typically, one or two substituents) selected from $(C_1-C_6)$alkyl, halogen, cyano, hydroxy, alkoxy, amino, —$CO_2H$, —$CO_2(C_1-C_4)$alkyl, —$C(O)NH_2$, —$C(O)NH(C_1-C_4)$alkyl, or —$C(O)N((C_1-C_4)$ alkyl$)_2$.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). A preferred aryl group is phenyl. When indicated as being "optionally substituted", the aryl groups may be unsubstituted or substituted with preferably one or more substituents (typically one to three substituents) selected from $(C_1-C_6)$alkyl, halogen, cyano, hydroxy, $(C_1-C_6)$alkoxy, amino, —$CO_2H$, —$CO_2(C_1-C_4)$alkyl, —$C(O)NH_2$, —$C(O)NH(C_1-C_4)$ alkyl, or —$C(O)N((C_1-C_4)$alkyl$)_2$. If substituted, substituted aryl groups include a chain of aromatic moieties (e.g., biphenyl, terphenyl, phenylnaphthalyl, etc.). The aryl group may be attached to the chemical entity or moiety by any one of the carbon atoms within the aromatic ring system.

The term "heteroaryl" or "aromatic heterocyclic ring" refers to aromatic moieties containing at least one heteratom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms selected from oxygen, sulfur and nitrogen and a typical fused heteroaryl ring system is a 9- to 10-membered ring system containing one to four heteroatoms selected from oxygen, sulfur and nitrogen. When indicated as being "optionally substituted", the heteroaryl group may be unsubstituted or substituted preferably with one of more substituents (typically, one or two substituents) selected from $(C_1-C_6)$alkyl, halogen, cyano, hydroxy, alkoxy, amino, —$CO_2H$, —$CO_2(C_1-C_4)$alkyl, —$C(O)NH_2$, —$C(O)NH(C_1-C_4)$alkyl, or —$C(O)N((C_1-C_4)$alkyl$)_2$. The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl).

The term "solvate" refers to a molecular complex of a compound represented by Formula (I) (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated by a NPY-5 receptor" or "modulation of a NPY-5 receptor" refers to the activation or deactivation of a NPY-5 receptor. For example, a ligand may act as an agonist, partial agonist, inverse agonist, antagonist, or partial antagonist.

As used herein, the term "antagonist" includes both full antagonists and partial antagonists, as well as inverse agonists.

The term "compounds of the present invention" (unless specifically identified otherwise) refer to compounds of Formula (IA), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

The present invention provides compounds and pharmaceutical formulations thereof that are useful in the treatment of diseases, conditions and/or disorders modulated by NPY-5 receptor antagonists.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1–19, Wiley, New York (1967–1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates.

For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Compounds of Formula (I) can be prepared using the general procedures outlined in Scheme I below.

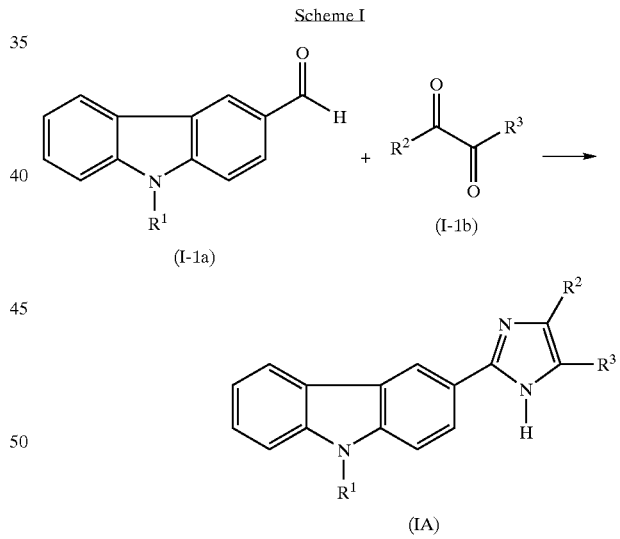

Compound (IA) may be prepared by heating the aldehyde I-1a with an appropriate 1,2-diketone in acetic acid with ammonium acetate at about 100° C. Suitable 1,2-diketones include 2,3-butandione, 1-phenyl-propane-1,2-dione, 1-pyridin-2-yl-propane-1,2-dione, and 3,3,3-trifluoro-1-pyridin-2-yl-propane-1,2-dione and the like.

Compounds of Formula (II) can also be prepared using the general procedures outlined in Scheme I below.

Scheme 2

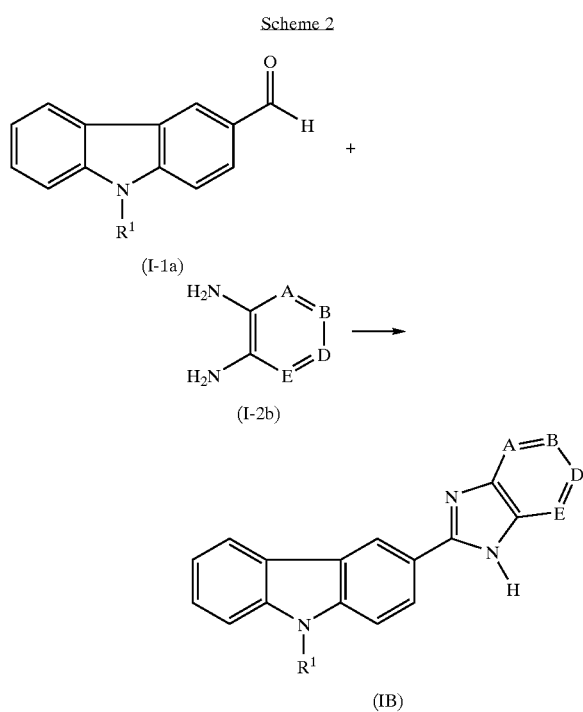

Compound IB may be formed directly by condensing the aldehyde I-1a with an appropriate 1,2-diamino substituted aryl or heteroaryl (wherein A, B, D, and E may be carbon or nitrogen, provided no more than two are nitrogen) ring I-2b by heating at about 100° C. to about 150° C. in a solvent such as nitrobenzene. Suitable diaminoaryl and heteroaryl rings include 1,2-diaminobenzene, 2,3-diaminopyridine, 3,4-diaminobenzoic acid, and 4,5-diaminopyrimidine.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, N-oxide, or prodrug with a suitable organic or inorganic acid and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulfonate salts, and the like. A preferred salt of the compounds of the present invention is the hydrochloride salt. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy) ethyl having from 5 to 8 carbon atoms, N-(alkoxycarbonyl) aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di ($C_1$–$C_2$) alkylcarbamoyl-($C_1$–$C_2$)alkyl and piperidino-, pyrrolidino- or morpholino($C_2$–$C_3$) alkyl.

Similarly, if a compound of the present invention contains an alcohol functional group, a prodrug can be formed by the replacement of the hydrogen atom of the alcohol group with a group such as ($C_1$–$C_6$)alkanoyloxymethyl, 1-(($C_1$–$C_6$) alkanoyloxy)ethyl, 1-methyl-1-(($C_1$–$C_6$)alkanoyloxy)ethyl, ($C_1$–$C_6$) alkoxycarbonyloxymethyl, N-($C_1$–$C_6$) alkoxycarbonylaminomethyl, succinoyl, ($C_1$–$C_6$)alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$–$C_6$)alkyl)$_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently ($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY' wherein Y' is H, ($C_1$–$C_6$)alkyl or benzyl, —C(OY$_0$)Y$_1$ wherein Y$_0$ is ($C_1$–$C_4$) alkyl and Y$_1$ is ($C_1$–$C_6$) alkyl, carboxy($C_1$–$C_6$)alkyl, amino($C_1$–$C_4$)alkyl or mono-N- or di-N,N-($C_1$–$C_6$)alkylaminoalkyl, —C(Y$_2$)Y$_3$ wherein Y$_2$ is H or methyl and Y$_3$ is mono-N- or di-N,N-($C_1$–$C_6$) alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention. Both the single positional isomers and mixture of positional isomers resulting from the N-oxidation of the pyrimidine and pyrazine rings are also within the scope of the present invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the compounds of the present invention may exist in different tautomeric forms, and all such forms are embraced within the scope of the invention. For example, all of the tautomeric forms of the imidazole moiety are included in the invention. Also, for example, all keto-enol and imine-enamine forms of the compounds are included in the invention.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The present invention further provides a method of treating diseases, conditions and/or disorders modulated by NPY-5 receptor antagonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders modulated by NPY-5 receptor antagonists. Investigations of NPY-5 antagonists have indicated that the following diseases, disorders and/or conditions are modulated by the NPY-5 receptor antagonists: obesity, feeding disorders (e.g., anorexia nervosa and bulimia nervosa), seizures, anxiety, diabetes, hypertension, hyperlipidemia, cancer (e.g., breast and pancreatic cancer), nasal congestion, sexual dysfunctions, congestive heart failure, intestinal dysfunctions, and psychiatric disorders (e.g., depression).

Accordingly, the compounds of the present invention described herein are useful in treating diseases, conditions, or disorders that are modulated by NPY-5 receptor antagonists. Consequently, the compounds of the present invention (including the compositions and processes used therein) may be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

It will also be understood by those skilled in the art that the compounds or the present invention, including pharmaceutical compositions and formulations thereof, can be used in a wide variety of combination therapies to treat the conditions and diseases described above. Thus, the compounds of the present invention can be used in conjunction with other pharmaceutical agents for the treatment of the disease/conditions described herein. For example, they may be used in combination with pharmaceutical agents that treat obesity, diabetes, hypertension, hyperlipidemia, cardiovascular disease, anxiety, depression, or psychosis. In combination therapy treatment, both the compounds of the present invention and the other drug therapies may be administered to mammals (e.g., humans, male or female, dogs, cats, horses) by conventional methods.

Any $\beta$-adrenergic agonist may be used as the second compound in the combination aspect of this invention. $\beta$-Adrenergic agents have been categorized into $\beta_1$, $\beta_2$, and $\beta_3$ subtypes. Agonists of $\beta$-receptors promote the activation of adenyl cyclase. Activation of $\beta_1$ receptors invokes increases in heart rate. Activation of $\beta_2$ receptors induces relaxation of smooth muscle tissue which produces a drop in blood pressure and the onset of skeletal muscle tremors. Activation of $\beta_3$ receptors is known to stimulate lipolysis, which is the breakdown of adipose tissue triglycerides to glycerol and fatty acids. Activation of $\beta_3$ receptors also stimulates the metabolic rate, thereby increasing energy expenditure. Accordingly, activation of $\beta_3$ receptors promotes the loss of fat mass. Compounds that stimulate $\beta$ receptors are therefore useful as anti-obesity agents. Compounds which are $\beta_3$-receptor agonists have hypoglycemic and/or anti-diabetic activity. Such activity is readily determined by those skilled in the art according to standard assays (International Patent Application, Publication No. WO 96/35671). Several compounds are described and referenced below; however, other $\beta$-adrenergic agonists will be known to those skilled in the art. International Patent Application, Publication No. WO 96/35671 (the disclosure of which is incorporated herein by reference) discloses compounds, such as substituted aminopyridines, which are $\beta$-adrenergic agonists. International Patent Application, Publication No. WO 93/16189 (the disclosure of which is incorporated herein by reference) discloses the use of selective $\beta_3$ receptor agonists in combination with compounds which modify eating behavior for the treatment of obestiy.

Any thyromimetic antiobesity agent may be used as the second compound in the combination aspect of this invention. These compounds are tissue selective thyroid hormone agonists. These compounds are able to induce weight loss by mechanisms other than appetite suppression, e.g., through stimulation of the metabolic rate in peripheral tissue, which, in turn, produces weight loss. Such metabolic effects are readily measured by those skilled in the art according to standard assays (for example, by indirect calorimetry). A variety of these compounds are described and referenced below, however other thyromimetic antiobesity agents will be known to those skilled in the art. It is well known to one of ordinary skill in the art that selectivity of thermogenic effect is an important requirement for a useful therapeutic agent in the treatment of, for example, obesity and related conditions. U.S. Pat. Nos. 5,401,772; 5,567,674; and 5,654,468, the disclosures of which are incorporated herein by reference, describe a series of heteroacetic acid derivatives.

Any eating behavior modifying compound may be used as the additional pharmaceutical agent. Compounds which modify eating behavior include anorectic agents, which are compounds which diminish the appetite. Such classes of anorectic agents are well known to one of ordinary skill in the art. A variety of these compounds are described and referenced above; however, other anorectic agents will be known to those skilled in the art and are described below. A particularly preferred monoamine reuptake inhibitor is sibutramine, which can be prepared as disclosed in U.S. Pat. No. 4,929,629, the disclosure of which is incorporated herein by reference. Preferred serotoninergic agents include fenfluramine and dexfenfluramine, which can be prepared as disclosed in U.S. Pat. No. 3,198,834, the disclosure of which is incorporated herein by reference. A particularly preferred dopamine agonist is bromocriptine, which can be prepared as disclosed in U.S. Pat. Nos. 3,752,814 and 3,752,888, the disclosures of which are incorporated herein by reference. Another preferred anorectic agent is phentermine, which can be prepared as disclosed in U.S. Pat. No. 2,408,345, the disclosure of which is incorporated herein by reference.

Any other NPY receptor antagonists may be used as the second component in the combination aspect of this invention. The term NPY receptor antagonist refers to compounds which interact with NPY receptors and inhibit the activity of neuropeptide Y at those receptors and thus are useful in treating disorders associated with neuropeptide Y, such as feeding disorders, including obesity. Such inhibition is readily determined by those skilled in the art according to standard assays. In addition, the compounds described and referenced below are NPY receptor antagonists; however, other NPY receptor antagonists will also be known to those skilled in the art. WO 99/07703 (the disclosure of which is hereby incorporated by reference) discloses certain 4-aminopyrrole (3,2-d) pyrimidines as neuropeptide Y receptor antagonists. Other such compounds are disclosed in the following WO publications the disclosures of which are hereby incorporated by reference: WO 96/14307; WO 96/40660; WO 98/03492; WO 98/03494; WO 98/03493; WO 96/14307; and WO 96/40660.

For the treatment of Alzheimer's disease, any cholinomimetic drug, such as Donepizil, may be used as the second compound in the combination aspect of this invention.

For the treatment of anxiety, any antianxiolytic drug, such as a benzodiazepine, valium, or librium, may be used as the second compound in the combination aspect of this invention.

For the treatment of depression, any tricyclic antidepressant such as, desipramine, or any selective serotonin reuptake inhibitor (SSRI's), such as ZOLOFT® and PROZAC®, may be used as the additional pharmaceutical agent in combination with a compound of the present invention.

For the treatment of psychosis, any typical or a typical antipsychotic drug, such as haloperidol or clozapine may be used as the additional pharmaceutical agent in combination with a compound of the present invention.

For the treatment of diabetes related diseases/conditions, any aldose reductase inhibitor may be used as the additional pharmaceutical agent in combination with a compound of the present invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, Diabetes, 29:861–864, 1980, "Red Cell Sorbitol, an Indicator of Diabetic Control"). A variety of aldose reductase inhibitors are described and referenced below; however other aldose reductase inhibitors will be known to those skilled in the art. An example of preferred aldose reductase inhibitor is zopolrestat.

For the treatment of diabetes related diseases/conditions, any glycogen phosphorylase inhibitor may be used as the additional pharmaceutical agent in combination with a compound of the present invention. The term glycogen phosphorylase inhibitor refers to any substance or agent or any combination of substances and/or agents which reduces, retards or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays described in the following publications which describe a variety of these compounds: WO 96/39384 and WO 96/39385, the disclosures of which are hereby incorporated herein by reference. Other preferred glycogen phosphorylase inhibitors are described above.

For the treatment of diabetes related diseases/conditions, any sorbitol dehydrogenase inhibitor may be used as the additional pharmaceutical agent in combination with a compound of the present invention. The term sorbitol dehydrogenase inhibitor refers to a compound which inhibits the enzyme sorbitol dehydrogenase, which catalyzes the oxidation of sorbitol to fructose. Such inhibition is readily determined by those skilled in the art according to standard assays (as described in U.S. Pat. No. 5,728,704 and references cited therein). A variety of these compounds are described and referenced below; however other sorbitol dehydrogenase inhibitors will be known to those skilled in the art. U.S. Pat. No. 5,728,704 (the disclosure of which is hereby incorporated by reference) discloses substituted pyrimidines to inhibit sorbitol dehydrogenase, lower fructose levels, and/or treat or prevent diabetic complications, such as diabetic neuropathy, diabetic retinopathy, diabetic nephropathy, diabetic microangiopathy and diabetic macroangiopathy. Other known or commercially marketed anti-diabetic compound may be used as the second compound in the practice of the combination therapy aspect of the present invention.

Neuropeptide Y (NPY) and related peptides (such as pancreatic polypeptide and peptide YY) are broadly distributed in central and peripheral neurons and have a broad array of biological activity mediated through the NPY receptors that exist in a variety of tissues. NPY (and related peptides) affect the cardiovascular system, vasculature, hormonal secretions, and central nervous system, renal, gastrointestinal and pulmonary systems and metabolism. NPY potently stimulates hyperphagia and induces insulin resistance. Investigations to date have implicated NPY in the pathophysiology of a number of diseases including feeding disorders, obesity, seizures, anxiety, diabetes, hypertension, cancer (e.g., breast and pancreatic cancer), nasal congestion, female or male sexual dysfunctions, congestive heart failure, and intestinal dysfunctions.

In addition, as a consequence of their action in reducing body fat (lipolysis), the compounds of the present invention may possess utility for increasing lean meat deposition and/or improving the lean meat to fat ratio in edible animals including poultry and ungulate animals such as swine, cattle, sheep, and goats. Compounds of the present invention can additionally be used for the treatment of obese household pets, for example companion animals such as dogs and cats.

Compounds of the present invention can be administered by any method which delivers the compound preferentially to the desired tissue (e.g., brain, renal or intestinal tissues). These methods include oral routes, parenteral, intraduodenal routes, etc. Generally, the compounds of the present invention are administered in single (e.g., once daily) or multiple doses or by constant infusion.

Generally, the compounds of the present invention are administered orally, or parenterally (e.g., intravenous, intramuscular, subcutaneous or intramedullary). Topical administration may also be indicated, for example, where the patient is suffering from swallowing disorders or whenever the medication is best applied to the surface of a tissue or organ as determined by the attending physician.

The amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

Thus, for example, in one mode of administration the compounds of this invention may be administered orally. The compounds of this invention may also be administered in a chronic daily mode.

Compounds of the present invention are dosed such that the amount used is effective for the indications described above (i.e., a therapeutically effective amount). A preferred dosage is about 0.001 to 100 mg/kg/day of the compound of this invention. An especially preferred dosage is about 0.01 to 50 mg/kg/day of the compound of the present invention.

When an additional pharmaceutical agent in administered in combination with a compound of the present invention, the additional pharmaceutical agent is generally dosed at a range between about 0.01 to about 100 mg/kg/day body weight, preferably about 0.1 mg/kg/day to about 10 mg/kg/day body weight. The combination may be administered singly or as a divided dose. Particularly, when the additional pharmaceutical agent is (1) sibutramine, the dosage of sibutramine is about 0.01 mg/kg/day to about 30 mg/kg/day body weight, preferably about 0.1 mg/kg/day to about 1 mg/kg/day body weight; (2) dexfenfluramine, the dosage of dexfenfluramine is about 0.01 mg/kg/day to about 30 mg/kg/day body weight, preferably about 0.1 mg/kg/day to about 1 mg/kg/day body weight; (3) bromocriptine, the dosage of bromocriptine is about 0.01 to about 10 mg/kg/day body weight, preferably 0.1 mg/kg/day to about 10 mg/kg/day body weight; (4) phentermine, the dosage of phentermine is about 0.01 mg/kg/day to about 10 mg/kg/day, preferably about 0.1 mg/kg/day to about 1 mg/kg/day body.

An effective amount of an aldose reductase inhibitor that may be used in the practice of the present invention is typically in the range of about 0.1 mg/kg/day to 100 mg/kg/day in single or divided doses, preferably 0.1 mg/kg/day to 20 mg/kg/day in single or divided doses.

In another embodiment of the present invention, the compounds of the present invention may be useful in the treatment of sexual dysfunction. Sexual dysfunction (SD) is a significant clinical problem, which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman, A. & Gingell, J. C., "The epidemiology and pathophysiology of erectile dysfunction," *J. Urology,* 161, 5–11 (1999)). FSD is best defined as the difficulty or inability of a woman to find satisfaction in sexual expression. Male sexual dysfunction (MSD) is generally associated with erectile dysfunction, also known as male erectile dysfunction (MED) (Benet et al, "Male Erectile dysfunction assessment and treatment options," *Comp. Ther.* 20, 669–673 (1994)).

The compounds of the invention may be particularly beneficial for the prophylaxis and/or treatment of sexual dysfunction in the male (e.g. male erectile dysfunction—MED) and in the female—female sexual dysfunction (FSD), e.g. female sexual arousal disorder (FSAD).

It is known that some individuals can suffer from male erectile dysfunction (MED). MED is defined as: "the inability to achieve and/or maintain a penile erection for satisfactory sexual performance" (NIH Consensus Development Panel on Impotence, 1993)"

It has been estimated that the prevalence of erectile dysfunction (ED) of all degrees (minimal, moderate and complete impotence) is 52% in men 40 to 70 years old, with higher rates in those older than 70 (Melman, A. & Gingell, J. C., "The epidemiology and pathophysiology of erectile dysfunction," *J. Urology,* 161, 5–11 (1999)). The condition has a significant negative impact on the quality of life of the patient and their partner, often resulting in increased anxiety and tension which leads to depression and low self esteem. Whereas two decades ago, MED was primarily considered to be a psychological disorder (Benet, A. E. et al, "Male erectile dysfunction assessment and treatment options," *Comp. Ther.* 20, 669–673, (1994)), it is now known that for the majority of patients there is an underlying organic cause. As a result, much progress has been made in identifying the mechanism of normal penile erection and the pathophysiology of MED.

Penile erection is a haemodynamic event which is dependent upon the balance of contraction and relaxation of the corpus cavernosal smooth muscle and vasculature of the penis (Lerner, S. E. et al, "A review of erectile dysfunction: new insights and more questions," *J. Urology,* 149, 1246–1255 (1993)). Corpus cavernosal smooth muscle is also referred to herein as corporal smooth muscle or in the plural sense corpus cavernosa. Relaxation of the corpus cavernosal smooth muscle leads to an increased blood flow into the trabecular spaces of the corpus cavernosa, causing them to expand against the surrounding tunica and compress the draining veins. This produces a vast elevation in blood pressure which results in an erection (Naylor, A. M., "Endogenous neurotransmitters mediating penile erection," *Br. J. Urology,* 81, 424–431 (1998)).

The changes that occur during the erectile process are complex and require a high degree of coordinated control involving the peripheral and central nervous systems, and the endocrine system (Naylor, 1998). Corporal smooth muscle contraction is modulated by sympathetic noradrenergic innervation via activation of postsynaptic $\alpha_1$ adrenoceptors. MED may be associated with an increase in the endogenous smooth muscle tone of the corpus cavernosum. However, the process of corporal smooth muscle relaxation is mediated partly by non-adrenergic, non-cholinergic (NANC) neurotransmission. There are a number of other NANC neurotransmitters found in the penis, other than NO, such as calcitonin gene related peptide (CGRP) and vasoactive intestinal peptide (VIP). The main relaxing factor responsible for mediating this relaxation is nitric oxide (NO), which is synthesized from L-arginine by nitric oxide synthase (NOS) (Taub, H. C. et al "Relationship between contraction and relaxation in human and rabbit corpus cavernosum," *Urology,* 42, 698–704 (1993)). It is thought that reducing corporal smooth muscle tone may aid NO to induce relaxation of the corpus cavernosum. During sexual arousal in the male, NO is released from neurones and the endothelium and binds to and activates soluble guanylate cyclase (sGC) located in the smooth muscle cells and endothelium, leading to an elevation in intracellular cyclic guanosine 3',5'-monophosphate (cGMP) levels. This rise in cGMP leads to a relaxation of the corpus cavernosum due to a reduction in the intracellular calcium concentration ($[Ca^{2+}]_i$), via unknown mechanisms thought to involve protein kinase G activation (possibly due to activation of $Ca^{2+}$ pumps and $Ca^{2+}$-activated $K^+$ channels).

The categories of female sexual dysfunction (FSD) are best defined by contrasting them to the phases of normal female sexual response: desire, arousal and orgasm (see S R Leiblum, (1998), Definition and Classification of Female Sexual Disorders, *Int. J. Impotence Res.,* 10, S104–S106). Desire or libido is the drive for sexual expression. Its manifestations often include sexual thoughts either when in the company of an interested partner or when exposed to other erotic stimuli. Arousal includes the vascular response to sexual stimulation, an important component of which is genital engorgement and increased vaginal lubrication, elongation of the vagina and increased genital sensation/sensitivity and a subjective excitement response. Orgasm is the release of sexual tension that has culminated during arousal. Hence, FSD occurs when a woman has an absent, inadequate or unsatisfactory response in any one or more of these phases, usually desire, arousal or orgasm.

The American Psychiatric Association classifies female sexual dysfunction (FSD) into four classes: FSAD, hypoactive sexual desire disorder (HSDD), female orgasmic disorder (FOD), and sexual pain disorders (e.g. dyspareunia and vaginismus) [see the American Psychiatric Association's Diagnostic and Statistical Manual of Mental Disorders, 4th Edition (DSM-IV)].

DSM-IV defines the four classes as follows:

HSDD—Persistently or recurrently deficient (or absent) sexual fantasies and desire for sexual activity. The judgment of deficiency or absence is made by the clinician, taking into account factors that affect functioning, such as age and the context of the persons life.

FSAD—Persistent or recurrent inability to attain, or to maintain until completion of the sexual activity, an adequate lubrication-swelling response of sexual excitement.

FOD—Persistent or recurrent delay in, or absence of, orgasm following a normal sexual excitement phase. Women exhibit wide variability in the type or intensity of stimulation that triggers orgasm. The diagnosis of FOD should be based on the clinician's judgment that the woman's orgasmic capacity is less than would be reasonable for her age, sexual experience, and the adequacy of the sexual stimulation she receives.

Sexual Pain Disorders such as Dyspareunia and Vaginismus. Dysparenuia—Recurrent or persistent genital pain associated with sexual intercourse. Vaginismus—Recurrent or persistent involuntary spasm of the musculature of the outer third of the vagina that interferes with sexual intercourse.

HSDD is present if a woman has no or little desire to be sexual, and has no or few sexual thoughts or fantasies. This type of FSD can be caused by low testosterone levels, due either to natural menopause or to surgical menopause. Other causes in both pre-menopausal woman (i.e. woman who are pre-menopausal and who have not have hysterectomies) as well as post-menopausal women include illness, medications, fatigue, depression and/or anxiety. Factors having a potential (conscious or sub-conscious) psychological impact such as relationship difficulties or religious factors may be related to the presence of/development of HSDD in females. The Diagnostic and Statistical Manual (DSM) IV of the American Psychiatric Association defines Female Sexual Arousal Disorder (FSAD) as being: ". . . a persistent or recurrent inability to attain or to maintain until completion of the sexual activity adequate lubrication-swelling response of sexual excitement. The disturbance must cause marked distress or interpersonal difficulty . . . ".

The arousal response consists of vasocongestion in the pelvis, vaginal lubrication and expansion and swelling of the external genitalia. The disturbance causes marked distress and/or interpersonal difficulty.

FSAD is a highly prevalent sexual disorder affecting pre-, peri- and post-menopausal (±hormone replacement therapy (HRT)) women. It is associated with concomitant disorders such as depression, cardiovascular diseases, diabetes and urogenital (UG) disorders. The primary consequences of FSAD are lack of engorgement/swelling, lack of lubrication and lack of pleasurable genital sensation. The secondary consequences of FSAD are reduced sexual desire, pain during intercourse and difficulty in achieving an orgasm. It has recently been hypothesized that there is a vascular basis for at least a proportion of patients with symptoms of FSAD (Goldstein et al., Int. J. Impot. Res., 10, S84–S90 (1998)) with animal data supporting this view (Park et al., Int. J. Impot. Res., 9, 27–37 (1997)).

Drug candidates for treating FSAD, which are under investigation for efficacy, are primarily erectile dysfunction therapies that promote circulation to male genitalia. They consist of two types of formulation, oral or sublingual medications (Apomorphine, Phentolamine, phosphodiesterase type 5 (PDE5) inhibitors, e.g. Sildenafil), and prostaglandin ($PGE_1$) that are injected or administered transurethrally in men and topically to the genitalia in women.

The compounds of the present invention may be advantageous by providing a means for restoring a normal sexual arousal response—namely increased genital blood flow leading to vaginal, clitoral and labial engorgement. This will result in increased vaginal lubrication via plasma transudation, increased vaginal compliance and increased genital sensitivity. Hence, the present invention provides a means to restore, or potentiate, the normal sexual arousal response.

By female genitalia herein we mean: "The genital organs consist of an internal and external group. The internal organs are situated within the pelvis and consist of ovaries, the uterine tubes, uterus and the vagina. The external organs are superficial to the urogenital diaphragm and below the pelvic arch. They comprise the mons pubis, the labia majora and minora pudendi, the clitoris, the vestibule, the bulb of the vestibule, and the greater vestibular glands" (Gray's Anatomy, C. D. Clemente, $13^{th}$ American Edition). R. J. Levin teaches us that because ". . . male and female genitalia develop embryologically from the common tissue anlagen, [that] male and female genital structures are argued to be homologues of one another. Thus the clitoris is the penile homologue and the labia homologues of the scrotal sac . . . " (Levin, R. J., Exp. Clin. Endocrinol., 98, 61–69 (1991)).

In summary, FSAD is characterized by inadequate genital response to sexual stimulation. The genitalia do not undergo the engorgement that characterizes normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants e.g. selective serotonin reuptake inhibitors (SSRIs) or antihypertensive agents.

FOD is the persistent or recurrent difficulty, delay in or absence of attaining orgasm following sufficient sexual stimulation and arousal, which causes personal distress.

Sexual pain disorders (includes dyspareunia and vaginismus) are characterized by pain resulting from penetration and sexual activity and may be caused by medications which reduce lubrication, endometriosis, pelvic inflammatory disease, inflammatory bowel disease or urinary tract problems.

According to a further aspect, the present invention additionally provides a method for the treatment and/or prevention of male sexual dysfunction (MSD), in particular male erectile dysfunction (MED) via treatment with a compound of the present invention as detailed hereinbefore.

According to a yet further aspect, the present invention additionally provides a method for the treatment and/or prevention of male sexual dysfunction via treatment with a combination of a compound of the present invention as defined hereinbefore and one or more compounds which inhibit the activity of PDE, in particular compounds which inhibit the activity of cGMP PDE5, and/or one or more compounds which inhibit the activity of NEP.

Men who display an insufficient response or lack of response to treatment with Viagra™ may benefit either from therapy based on treatment with compounds of the present invention alone or via combination therapy based on compound(s) of the present invention and a cGMP PDE5i, such as for example sildenafil. Patients with mild to moderate MED should benefit from combined treatment based on compound(s) of the present invention alone or in combination with a NEPi, and patients with severe MED may also respond. Mild, moderate and severe MED will be terms well-known to those skilled in the art, but guidance can be found in: The Journal of Urology, 151, 54–61 (1994).

MED patient groups, which are described in more detail in Clinical Andrology, 23(4), p773–782, and chapter 3 of the book by I. Eardley and K. Sethia "Erectile Dysfunction—Current Investigation and Management, published by Mosby-Wolfe, are as follows: psyhcogenic, endocrinologic, neurogenic, arteriogenic, drug-induced sexual dysfunction (lactogenic) and sexual dysfunction related to cavernosal factors, particularly venogenic causes.

Suitable cGMP PDE5 inhibitors for the use in combination with a compound of the present invention for the treatment of MED according to the present invention include: the pyrazolo [4,3-d]pyrimidin-7-ones disclosed in EP-A-0463756; the pyrazolo [4,3-d]pyrimidin-7-ones disclosed in PCT Publication No. WO 01/27112; the pyrazolo [4,3-d]pyrimidin-7-ones disclosed in PCT Publication No. WO 01/27113; the indole-1,4-diones disclosed in WO95/19978 and the triazin-4-ones disclosed in PCT Publication No. WO99/24433.

More preferred are compounds such as, 5-[2-ethoxy-5-(4-methyl-1-piperazinylsulphonyl) phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimid in-5-yl)-4-ethoxyphenyl]sulphonyl]-4-methylpiperazine (see, EP-A-0463756);

5-[2-ethoxy-5-(4-ethyl piperazin-1-ylsulphonyl)pyridin-3-yl]-3-ethyl-2-[2-methoxyethyl]-2,6-dihydro-7H-pyrazolo [4,3-d]pyrimid in-7-one, also known as 1-{6-ethoxy-5-[3-ethyl-6,7-dihydro-2-(2-methoxyethyl)-7-oxo-2H-pyrazolo [4,3-d]pyrimidin-5-yl]-3-pyridylsulphonyl}-4-ethylpiperazine (see, WO 01/27113, Example 8);

5-(5-Acetyl-2-butoxy-3-pyrid inyl)-3-ethyl-2-(1-ethyl-3-azetidinyl)-2,6-dihydro-7H-pyrazolo[4,3-d]pyrimidin-7-one (see, WO 01/27112, Example 132);

(6R,12aR)-2,3,6,7,12,12a-hexahydro-2-methyl-6-(3,4-methylenedioxyphenyl)-pyrazino[2',1':6,1]pyrido[3,4-b] indole-1,4-dione (IC-351, tadalafil), i.e. the compound of Examples 78 and 95 in PCT Publication No. WO95/19978, as well as the compound of Examples 1, 3, 7 and 8; and 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil) also known as 1-[[3-(3,4-dihydro-5-methyl-4-oxo-7-propyl imidazo[5,1-f]-as-triazin-2-yl)-4-ethoxyphenyl]sulphonyl]-4-ethylpiperazine (i.e. the compound of Examples 20, 19, 337 and 336 in PCT Publication No. WO 99/24433);
and pharmaceutically acceptable salts thereof.

According to a further aspect the present invention provides a composition for the treatment of MED comprising a compound of the present invention and sildenafil.

The suitability of any particular cGMP PDE5 inhibitor for use in combination with a compound of the present invention can be readily determined by evaluation of its potency and selectivity using literature methods followed by evaluation of its toxicity, absorption, metabolism, pharmacokinetics, etc in accordance with standard pharmaceutical practice.

Preferred CGMP PDE5 inhibitors for use herein have an $IC_{50}$ at less than 100 nanomolar, more preferably, at less than 50 nanomolar, more preferably still at less than 10 nanomolar. Preferably the cGMP PDE5 inhibitors for use in the pharmaceutical combinations according to the present invention are selective for the PDE5 enzyme. Preferably they have a selectivity of PDE5 over PDE3 of greater than 100 more preferably greater than 300. More preferably the PDE5 has a selectivity over both PDE3 and PDE4 of greater than 100, more preferably greater than 300.

Selectivity ratios may readily be determined by the skilled person. $IC_{50}$ values for the PDE3 and PDE4 enzyme may be determined using established literature methodology, see S A Ballard et al, *Journal of Urology*, 159, 2164–2171 (1998).

Preferred herein are NEP inhibitors wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, candoxatril, candoxatrilat, sampatrilat). Suitable NEP inhibitor compounds are described in EP-A-1097719.

Particularly preferred NEPi compounds for as auxiliary agents for use in the treatment of MED according to the present invention are those described in PCT Publication No. WO 02/079143 (Application No. PCT/IB02/00807, filed Mar. 18, 2002).

Especially preferred is (S)-2-[(1-{[3-(4-chlorophenyl) propyl]-carbamoyl}cyclo-pentyl)methyl]-4-methoxybutanoic acid or a pharmacuetically acceptable salt such as the sodium salt thereof as detailed at Example 22 in PCT Publication No. 02/079143.

According to a further aspect the present invention provides a composition for the treatment of MED comprising a compound of the present invention and (S)-2-[(1-{[3-(4-chlorophenyl)propyl]carbamoyl}cyclopentyl)methyl]-4-methoxybutanoic acid.

According to yet a further aspect of the present invention, there is provided use of a compound of the present invention for the treatment of female sexual dysfunction (FSD).

According to another aspect of the present invention, there is provided use of a compound of the present invention and one or more additional active agents for the treatment of female sexual dysfunction (FSD).

Preferably, the one or more additional active agents is/are selected from the group consisting of:

1) estrogen receptor modulators and/or estrogen agonists and/or estrogen antagonists;
2) testosterone replacement agent and/or testosternone (Tostrelle) and/or dihydrotestosterone and/or dehydroepiandrosterone (DHEA) and/or a testosterone implant;
3) estrogen, estrogen and medroxyprogesterone or medroxyprogesterone acetate (MPA) (as a combination), or estrogen and methyl testosterone hormone replacement therapy agent;
4) one or more dopaminergic agents;
5) one or more 5HT agonists
6) one or more of a melanocortin receptor agonist or modulator or melanocortin enhancer;
7) one or more of an NEP (neutral endopeptidase) inhibitor;
8) one or more of a PDE (phosphodiesterase) inhibitor; and
9) one or more of a bombesin receptor antagonist or modulator.

Preferably, said FSD is female sexual arousal disorder (FSAD). Alternatively, said FSD is female orgasmic disorder (FOD). In a further alternative, said FSD is hypoactive sexual desire disorder (HSDD). In yet a further alternative, said FSD is a sexual pain disorder, preferably Dyspareunia or Vaginismus.

Examples of estrogen receptor modulators and/or estrogen agonists and/or estrogen antagonists, include raloxifene or lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof (compound (a) below), the preparation of which is detailed in WO 96/21656.

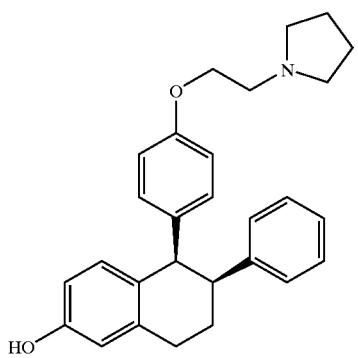

Compound (a)

An example of a testosterone replacement agent is dehydroandrostendione.

Examples of hormone replacement therapy agent include Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, and Tibolone.

Examples of dopaminergic agents include apomorphine or a selective D2, D3 or D2/$D_3$agonist such as, pramipexole and ropirinol (as claimed in WO-0023056), L-Dopa or carbidopa, PNU95666 (as disclosed in WO-0040226).

Examples of additional NPY (neuropeptide Y) inhibitors include NPY1 or NPY5 inhibitors, preferably NPY1 inhibitor. Preferably, said NPY inhibitors (including NPY Y1 and NPY Y5) having an IC50 of less than 100 nM, more preferably less than 50 nM. Suitable NPY, and in particular NPY1 inhibitor compounds, are described in EP-A-1097718.

Examples of 5HT2c receptor agonists include pyrazine and pyrimidine derivatives such as those described in PCT Application Nos. PCT/IB02/02293 and PCT/IB02/02261 both filed on Jun. 17, 2002; PCT Publication No. WO 02/40456 and U.S. Pat. No. 6,465,467.

Examples of a melanocortin receptor agonist or modulator or melanocortin enhancer include melanotan 11, PT-14, PT-141 or compounds disclosed in WO-09964002, WO-00074679, WO-09955679, WO-00105401, WO-00058361, WO-00114879, WO-00113112 or WO-09954358.

Suitable NEP inhibitors are as described hereinabove.

According to a further aspect, the present invention provides a composition for the treatment of FSD comprising a compound of the present invention and (S)-2-[(1-{[3-(4-chlorophenyl)propyl]carbamoyl}cyclopentyl)methyl]-4-methoxybutanoic acid.

Preferred PDE inhibitors include a PDE 2, 3, 4, 5, 7 or 8 inhibitor, preferably PDE2 or PDE5 inhibitor and more preferably a PDE5 inhibitor (as described hereinabove), most preferably sildenafil.

According to a further aspect, the present invention provides a composition for the treatment of FSD comprising a compound of the present invention and sildenafil.

Preferred examples of one or more of bombesin receptor antagonists or modulators would be antagonists or modulators for $BB_1$, including those described in PCT Publication No. WO 02/40008 (Application No. PCT/GBO1/05018, filed 14 Nov. 2001) and PCT Publication No. WO 02/40022 (Application No. PCT/GB00/04380, filed 17 Nov. 2000). Also preferred are bombesin $BB_2$, $BB_3$, or $BB_4$ receptor antagonists. Preferred bombesin receptor antagonists are also mentioned as "auxiliary agents" in PCT Publication No. WO 02/47670.

It should be noted that a full list of possible "additional active agents" can be found in PCT Publication No. WO 02/47670—and are described as "auxiliary agents" therein.

The compounds of the present invention are generally administered in the form of a pharmaceutical composition comprising at least one of the compounds of this invention together with a pharmaceutically acceptable carrier, vehicle or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions, for example, in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Other administration methods include iontophoretic patches, implants and inhalation.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 or 500 (available from Varian Inc., Palo Alto, Calif.) at room temperature at 400 and 500 MHz 1H, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet; 2s, two singlets. In some cases only representative $^1$H NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer equipped with Gilson 215 liquid handling system and HP 1100 DAD was used to carry out the experiments.

Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and only the lower mass ion is given. MS peaks are reported for all examples.

Column chromatography was performed with either Baker™ silica gel (40 μm; J. T. Baker, Phillipsburg, N.J.) or Silica Gel 50 (EM Sciences™, Gibbstown, N.J.) in glass columns or in Biotage™ columns (ISC, Inc., Shelton, Conn.) under low nitrogen pressure. Radial chromatography was performed using a Chromatotron™ (Harrison Research).

9-Ethyl-9H-carbazole-3-carbaldehyde is available from Sigma-Adlrich (St. Louis, Mo.).

Example 1

Preparation of 9-Ethyl-3-(5-methyl-4-phenyl-1H-imidazol-2-yl)-9H-carbazole (1A):

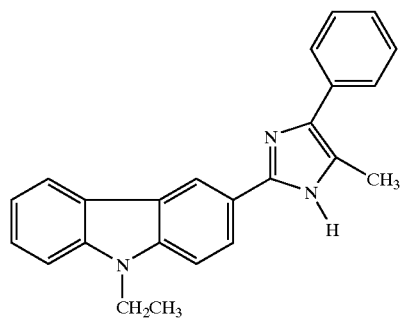

A solution of 9-ethyl-9H-carbazole-3-carbaldehyde (500 mg, 2.23 mmol) and 1-phenyl-1,2-propanedione (0.3 ml, 2.23 mmol) were dissolved in glacial acetic acid (5 ml). Ammonium acetate (410 mg, 5.37 mmol) was added in one portion, and the resultant mixture was heated at 100° C. for 4h. The reaction mixture was cooled to room temperature. Saturated aqueous sodium carbonate was added until the pH of the reaction mixture was neutral, and 1 N aqueous sodium hydroxide was added until the pH was ca. 10. The reaction mixture was then extracted with dichloromethane, and the organic extracts were dried over anhydrous magnesium sulfate and concentrated. Purification of the product by preparatory thin-layer chromatography (20% ethyl acetate in hexanes, plate developed twice) provided the title compound 1A (35 mg):

$^1$H-NMR (400 MHz, CD$_3$OD); δ 1.38 (t, 3H); 2.44 (s, 3H); 4.41 (q, 2H); 7.21 (app t, 1H), 7.30 (app t, 1H); 7.45 (m, 4H); 7.55 (d, 1H); 7.62 (d, 2H); 8.00 (d, 1H); 8.12 (d, 1H); 8.62 (d, 1H); MS m/z 352.2 (MH$^+$).

The following compounds were prepared in accordance with procedures analogous to those given in Example 1 for the preparation of Compound 1A using the appropriate starting material.

Example 2

Preparation of 9-ethyl-3-(4-phenyl-5-trifluoromethyl-1H-imidazol-2-yl)-9H-carbazole (2A):

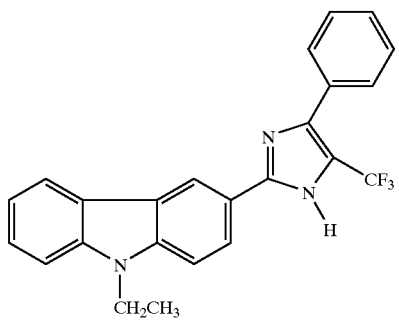

MS m/s 406.2 (M$^+$+1).

Example 3

Preparation of 9-ethyl-3-(5-methyl-4-pyridin-2-yl-1H-imidazol-2-yl)-9H-carbazole (3A):

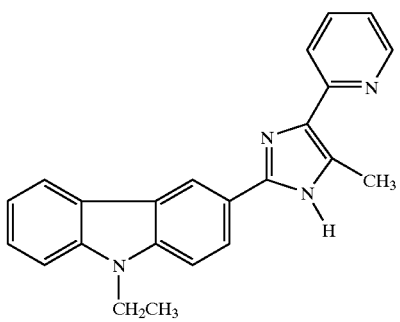

MS m/s 353.2 (M$^+$+1).

Example 4

Preparation of 3-(4,5-dimethyl-1H-imidazol-2-yl)-9-ethyl-9H-carbazole (4A):

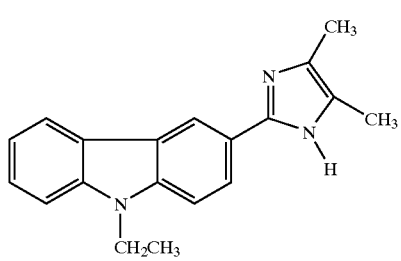

4A

MS m/s 290.2 (M$^+$+1).

Example 5

Preparation of 9-Ethyl-3-(1H-imidazo[4,5-c]pyridin-2-yl)-9H-carbazole (5A):

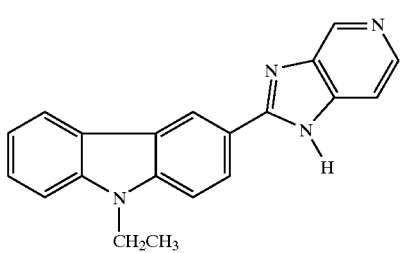

5A

A mixture of 9-ethyl-9H-carbazole-3-carbaldehyde (444 mg, 1.99 mmol) and 3,4-diaminopyridine (217 mg, 1.99 mmol) in nitrobenzene (1.5 ml) was heated at 145° C. for 24 hours. The reaction mixture was cooled to room temperature and purified directly by flash column chromatography (0.1% ammonium hydroxide/5% methanol/dichloromethane) to afford the title compound 5A (94 mg):

$^1$H-NMR (400 MHz, CD$_3$OD); δ 1.43 (t, 3H); 4.48 (q, 2H); 7.28 (t, 1H); 7.49 to 7.62 (br m, 3H); 7.68 (d, 1H); 8.19 (d, 1H); 8.25 (d, 1H); 8.29 (d, 1H); 8.86 (d, 2H); and MS m/s 313.3 (M$^+$+1).

The following compounds were prepared in accordance with procedures analogous to those given in Example 5 for the preparation of Compound 5A using the appropriate starting material.

Example 6

Preparation of 3-(1H-benzoimidazol-2-yl)-9-ethyl-9H-carbazole (6A):

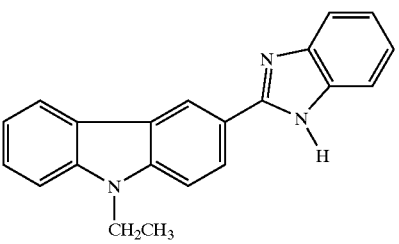

6A

MS m/s 312.1 (M$^+$+1).

Example 7

Preparation of 9-ethyl-3-(3H-imidazo[4,5-b]pyridin-2-yl)-9H-carbazole (7A):

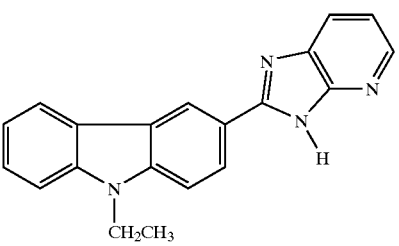

7A

MS m/s 313.2 (M$^+$+1).

Example 8

Preparation of 9-ethyl-3-(7H-Purin-8-yl)-9H-carbazole (8A):

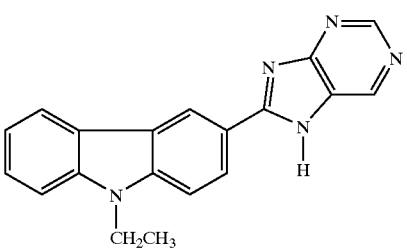

8A

MS m/s 314.2 (M$^+$+1).

Example 9

Preparation of 2-(9-ethyl-9H-carbazol-3-yl)-1H-benzoimidazole-5-carboxylic acid (9A):

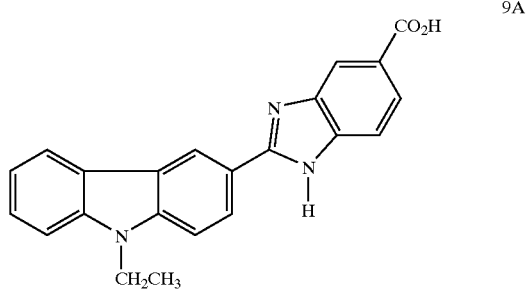

MS m/s 356.2 (M$^+$+1).

Pharmacological Testing

The utility of the compounds of the present invention in the practice of the instant invention can be evidenced by activity in at least one of the protocols described hereinbelow. For example, obesity in patients or to induce weight loss or for anorectic activity is demonstrated by the activity of the compounds of the present invention in conventional preclinical assays described below. Such assays also provide a means whereby the activities of the compounds of the present invention can be compared with the activities of other known compounds. The results of these comparisons are useful for determining dosage levels in mammals, including humans, for the treatment of such diseases.

Assay for NPY-5 Binding

[$^{125}$I] peptide YY (PYY) Binding at Human NPY Receptors Expressed in Sf9 Cells:

Baculovirus-infected Sf9 cells (American Tissue Culture Collection, ACTT, Rockville, Md.) expressing recombinant human NPY 5 receptors are harvested at 48 hours. h NPY-Y5 receptor cDNA is cloned using standard cloning techniques. (Ref: *Molecular Cloning A Laboratory Manual*, 2nd Edition, J. Sambrook, E. F. Fritsch, T. Maniatis; Cold Spring Habor Laboratory Press; Cold Spring Habor, N.Y., 1989) and cells were transfected using calcium phosphate. At the time of harvest, cells pellets are resuspended in lysis buffer (20 mM Tris-HCl, pH 7.4, 5 mM EDTA, 0.5 ug/ml leupeptin, 2 ug/ml Aprotonin and 200 mM PMSF) and homogenized using a Polytron (setting 3, 25–30 seconds). Homogenates are centrifuged at 4° C. for 5 minutes at 200×g (~1.5 rpm) to pellet the nuclei. The supernatant is collected into a fresh tube and centifuged at 48,000×g for 10 minutes. Pellets are washed once in lysis buffer and centrifuged. The final pellet is resuspended in phosphate buffered saline (PBS) and stored in aliquots at −80° C. Purified membranes are washed using PBS and resuspended in binding buffer (50 mM Tris(HCl), pH 7.4, 5 mM KCl, 120 mM NaCl 2 mM CaCl$_2$, 1 mM MgCl$_2$ 0.1% bovine seurm albumin (BSA)). Membranes (20 ug/reaction tube) are added to polypropylene tubes containing 0.035 nM [$^{125}$I]PYY(porcine) (Dupont New Research Products, Boston Mass.), compounds ranging from 10$^{-12}$ M to 10$^{-5}$ M, and buffer to yield a final volume of 0.5 mL. Nonspecific binding is determined in the presence of 1 uM NPY(human) (Sigma; St. Louis, Mo.) and accounts for 10% of total binding. Following a 2 hour incubation at room temperature, the reaction is terminated by rapid vacuum filtration. Samples are filtered over pre-soaked GF/C Whatman filters (1.0% polyethylenemine) and rinsed 2 times with 5 mL cold binding buffer without BSA. A gamma counter is used to count filters with an efficiency of 85%. IC$_{50}$ values are calculated with the non-linear curve fitting program RS/1 (SigmaPlot, Jandel).

Table 1 below provides representative examples of the binding data observed for some of the compound exemplified in the Examples above.

TABLE 1

| Example No. | Avg. Y5 Ki, nM (n) |
|---|---|
| 1A | 15 (4) |
| 3A | 101 |
| 4A | 10 (2) |
| 5A | 15 (2) |
| 7A | 1.5 (2) |
| 8A | 8 (2) |

Y5 Ca Mobilization Assay

A stable Bowes melanoma cell line is generated expressing functional Y5 receptors useful for the secondary screening of Y5 antagonists using a calcium fluorescence assay.

The coding sequence for human Y5 receptor h NPY-Y5 receptor cDNA is cloned using standard cloning techniques (Ref: *Molecular Cloning A Laboratory Manual*, 2nd Edition, J. Sambrook, E. F. Fritsch, T. Maniatis; Cold Spring Habor Laboratory Press; Cold Spring Habor, N.Y., 1989) and is subcloned into a novel mammalian expression vector called pM$^2$ (Ref: B. S. Sachais et al., *J. Biol. Chem.*, 1998, 266:2319–2322). This expression vector has a Harvey murine sarcoma virus long terminal repeat to drive expression of the Y5 structural gene. This plasmid construct is used along with calcium phosphates to stably transfect human Bowes melanoma cells (HMCB; obtained from ATCC, Rockville, Md.), a cell line in which several G☐i-linked receptors are expressed at reasonable levels and are coupled to functional responses. Cells are maintained at 37° C. and 5% CO$_2$ in Eagle's minimum essential medium with 0.1 mM non-essential amino acids, 1.0 mM sodium pyruvate and 25 mM HEPES which is supplemented with 10% fetal bovine serum (pH 7.3). This cell host exhibits low levels of Y1 responses and sites, and no other NPY-induced responses. The Y1 antagonist BIBP3226 (Research Biochemicals International, Natick, Mass.) at 10 uM completely blocks the endogenous NPY response. A single clonal cell line is isolated and characterized with the agonist peptide NPY. In the presence of 10 uM BIBP3226, NPY stimulated calcium mobilization with an EC$_{50}$ from 9 nM to 54 nM in ten independent studies.

Cells are plated onto 96 well plates at 30,000 cells/well for twenty-four hours. The cells are rinsed with buffered saline (consisting of: 115 mM NaCl, 0.96 mM NaH$_2$PO$_4$, 1 mM MgSO$_4$, 25 mM HEPES, 2 mM CaCl$_2$, 5 mM KCl, 5 mM Glucose, 1 mM Probenecid) and incubated for 1.5 hrs. in the fluorescent Ca$^{2+}$ indicator Fluo-3 AM (10 $\mu$M, Teflabs, Austin, Tex.) made in the same buffered saline. Cells are rinsed twice with buffer supplemented with 1 mM carbachol and 10 $\mu$M BIBP3226. NPY applied to HMCB Y5 cells produce a concentration dependent increase in intracellular calcium as determined by an increase in fluorescence read on a Fluorometric Imaging Plate Reader (FLIPR, Molecular Devices, Sunnyvale, Calif.). The concentration of NPY used in these experiments is between the EC$_{30}$ and EC$_{50}$ as determined just prior to each experiment. Fluorescence increase in response to NPY in the presence of test compounds was compared to control responses in the same plate and the $IC_{50}$ for each compound is determined by a fit of the data to the logistic equation (Kaleidograph software, Reading Pa.).

PYY 3-36 Induced $GTP\gamma^{35}S$ Binding at Human NPY Y5 Receptors Co-Expressed with $G\alpha O$, $G\beta 1$, and $G\gamma 2$ in Sf9 Cells.

Agonist induced $GTP\gamma^{35}S$ binding by G-protein coupled receptors (GPCR) provides a functional measure of G-protein activation. This assay has been widely used for many GPCR's and offers the possibility to distinguish agonists from antagonists and to determine potency and efficacy of agonists for a given GPCR (Thomas et al., 1995; O'Boyle and Lawler, 1995). $GTP\gamma^{35}S$ binding activity is measured using a modification of a previously described method (Wieland and Jacobs, 1994). Log-phase Sf9 cells (ATCC, Rockville, Md.) are co-infected with separate baculoviral stocks encoding the hNPY Y5 (cloned using standard cloning techniques (Ref: *Molecular Cloning A Laboratory Manual,* 2nd Edition, J. Sambrook, E. F. Fritsch, T. Maniatis; Cold Spring Habor Laboratory Press; Cold Spring Habor, N.Y., 1989) receptor and the G-protein subunits $\alpha o\beta 1$ and $\gamma 2$ (purchased from BioSignal Montreal, Canada) followed by culturing in Hink's TNM-FH insect medium supplemented Grace's with 4.1 mM L-Gln, 3.3 g/L LAH, 3.3 g/L ultrafiltered yeastolate and 10% heat-inactivated fetal bovine serum at 27° C. 72 hours post infection, a sample of cell suspension is analyzed for viability by trypan blue dye exclusion, and the remaining Sf9 cells are harvested via centrifugation (3000 rpm/10 min/4° C.). Each pellet is resuspended in homogenization buffer (10 mM HEPES, 250 mM sucrose, 0.5 µg/ml leupeptin, 2 µg/ml Aprotonin, 200 µM PMSF and 2.5 mM EDTA, pH 7.4) and homogenized using a Polytron (setting 5 for 30 seconds). The homogenate is centrifuged at 4° C. for 10 minutes at 536×g to pellet the nuclei. The supernatant is collected into a fresh tube and centrifuged twice in the same buffer at 48,000×g for 40 minutes. The final pellet for each membrane preparation is resuspended in DPBS containing 5 mM EDTA and stored in aliquots at −80° C. On the day of the assay, thawed membrane homogenates are resuspended in assay buffer (50 mM Tris pH 7.0,120 mM NaCl, 2 mM $MgCl_2$, 2 mM EGTA, 0.1% BSA, 0.1 mM bacitracin, 100KIU/mL Aprotinin, 5 µM GDP) and added to reaction tubes at a concentration of 30 mg/reaction tube. After adding test compounds at concentrations ranging from $10^{-11}M$ to $10^{-5}M$, reactions are initiated by the addition of both 100 pM $GTP\gamma^{35}S$ and PYY 3–36 ranging in concentration from 0.001 nM to 1.0 µM (final volume of 0.250 ml). Following a 30 minute incubation at RT, the reaction is terminated by vacuum filtration over GF/C filters (Pre-soaked in wash buffer, 0.1% BSA) with ice-cold wash buffer (50 mM Tris pH 7.0,120 mM NaCl). Bound $GTP\gamma^{35}S$ is determined by liquid scintillation spectrometry. Non-specific binding is defined by 10 mM GTPγS. To estimate the $EC_{50}$, $IC_{50}$ and $K_i$, the results of $GTP\gamma^{35}S$ binding experiments are analyzed using SigmaPlot software (Jandel).

In Vivo Methods

Single Dose Effects on Food and Water Intake and Body Weight Gain in Fasted Rats Subjects. Male Sprague-Dawley rats (Sasco, St. Louis, Mo.) weighing 210–300 g at the beginning of the experiment are used. Animals are triple-housed in stainless steel hanging cages in a temperature (22° C.±2°) and humidity (40–70% RH) controlled animal facility with a 12:12 hour light-dark cycle. Food (Standard Rat Chow, PMI Feeds Inc., #5012) and water are available ad libitum.

Apparatus. Consumption data is collected while the animals are housed in Nalgene Metabolic cages (Model #650-0100). Each cage is comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment.

The second assemby includes a water bottle support, a PC water bottle (100 ml capacity) and a graduated water spillage collection tube. The water bottle support funnels any spilled water into the water spillage colllection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, and body weight are measured with an Ohaus Portable Advanced scale (±0.1 g accuracy).

Procedure. Prior to the day of testing, animals are habituated to the testing apparatus by placing each animal in a Metabolic cage for 1 hour. On the day of the experiment, animals that are food deprived the previous night are weighed and assigned to treatment groups. Assignments are made using a quasi-random method utilizing the body weights to assure that the treatment groups have similar average body weight. Animals are then administered either vehicle (generally 0.5% methyl cellulose, MC) or test compound. At that time, the feeding drawer filled with pulverized chow, the filled water bottle, and the empty urine and feces collection tubes are weighed. Two hours after test compound treatment, each animal is weighed and placed in a Metabolic Cage. Following a one hour test session, animals are removed and body weight obtained. The food and water containers are then weighed and the data recorded.

Test Compound. Test Compound (suspended in 0.5% MC) or 0.5% MC is administered orally (0.1–50 mg/kg for oral (PO) dosing) using a gavage tube connected to a 3 or 5 ml syringe at a volume of 10 ml/kg. In some instances test compound is administered by a systemic route (e.g. by intravenous injection 0.1–20 mg/kg for i.v. dosing). Test compound for oral dosing is made into a homogenous suspension by stirring and ultrasonicating for at least 1 hour prior to dosing.

Statistical Analyses. The means and standard errors of the mean (SEM) for food consumption, water consumption, and body weight change are calculated. One-way analysis of variance using Systat (5.2.1) is used to test for group differences. A significant effect is defined as having a p value of <0.05.

The following parameters are defined: Body weight change is the difference between the body weight of the animal immediately prior to placement in the metabolic cage and its body weight at the end of the one hour test session. Food consumption is the difference in the weight of the food drawer prior to testing and the weight following the 1 hour test session. Water consumption is the difference in the weight of the water bottle prior to testing and the weight following the 1 hour test session.

Overnight Food Intake

Subjects. Male Sprague-Dawley rats (Sasco, St. Louis, Mo.) weighing 210–300 g at the beginning of the experiment are used. Animals are pair or triple-housed in stainless steel hanging cages in a temperature (22° C.±2°) and humidity (40–70% RH) controlled animal facility with a 12:12 hour light-dark cycle. Food (Standard Rat Chow, PMI Feeds Inc., #5012) and water are available ad libitum.

Apparatus. Consumption and elimination data are obtained while the animals are housed in Nalgene Metabolic cages (Model #650-0100). Each cage is comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment. The second assembly includes a water bottle support, a PC water bottle (100 ml capacity) and a graduated water spillage collection tube. The water bottle support funnels any spilled water into the water spillage collection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, urine excretion, feces excretion, and body weight are measured with an Ohaus Portable Advanced scale (±0.1 g accuracy).

Procedure. On the day of the experiment, animals are weighed and assigned to treatment groups. Assignments are made using a quasi-random method utilizing the body weights to assure that the treatment groups have similar average body weight. Two hours prior to lights off (1830 hours), animals are administered either vehicle (0.5% methyl cellulose, MC) or test compound. At that time, the feeding drawer filled with pulverized chow, the filled water bottle, and the empty urine and feces collection tubes are weighed. Following dosing, each animal is weighed and placed in the Metabolic Cage. Animals are removed from the Metabolic Chamber the following morning (0800 hours) and body weight obtained. The food and water containers, and the feces and urine collection tubes, are weighed and the data recorded.

Test Compound. Test compound (suspended in 0.5% MC) or 0.5% MC is administered orally (PO) using a gavage tube connected to a 3 or 5 ml syringe at a volume of 10 ml/kg. Test compound is made into a homogenous suspension by stirring and ultrasonicating for at least 1 hour prior to dosing. In some experiments, animals are tested for more than 1 night. In these studies, animals are administered, on subsequent nights, the same treatment (test compound or 0.5% MC) they had received the first night.

Statistical Analyses. The means and standard errors of the mean (SEM) for food consumption, water consumption, urine excretion, feces excretion, and body weight change were calculated. One-way analysis of variance using Systat (5.2.1) is used to test for group differences. A significant effect is defined as having a p value of <0.05.

The following parameters are defined: Body weight change is the difference between the body weight of the animal immediately prior to placement in the metabolic cage (1630 hours) and its body weight the following morning (0800 hours). Food consumption is the difference in the weight of the food drawer at 1630 and the weight at 0800. Water consumption is the difference in the weight of the water bottle at 1630 and the weight at 0800. Fecal excretion is the difference in the weight of the empty fecal collection tube at 1630 and the weight at 0800. Urinary excretion is the difference in the weight of the empty urine collection tube at 1630 and the weight at 0800.

What is claimed is:

1. A compound of Formula (IA)

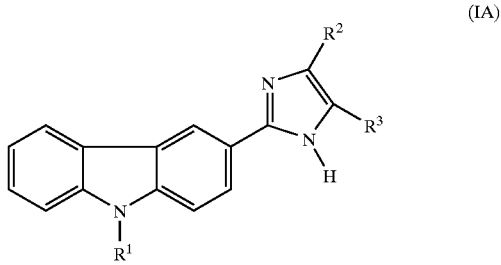

wherein

R$^1$ is hydrogen or (C$_1$–C$_4$)alkyl;

R$^2$ is hydrogen, (C$_1$–C$_4$)alkyl, aryl, or a 5–6 membered heteroaryl containing one to three heteroatoms selected from oxygen, nitrogen or sulfur; and R$^3$ is hydrogen, (C$_1$–C$_4$)alkyl or halo-substituted (C$_1$–C$_4$)alkyl;

or R$^2$ and R$^3$ taken together form an optionally substituted aromatic six-membered heterocyclic ring, where said heterocyclic ring contains 1 to 2 nitrogen ring atoms, or an optionally substituted aromatic six-membered carbocyclic ring;

a pharmaceutically acceptable salt thereof, a prodrug of said compound or said salt, or a solvate or hydrate of said compound, said salt or said prodrug.

2. The compound of claim 1 selected from the group consisting of 9-ethyl-3-(5-methyl-4-phenyl-1H-imidazol-2-yl)-9H-carbazole;

9-ethyl-3-(4-phenyl-5-trifluoromethyl-1H-imidazol-2-yl)-9H-carbazole;

9-ethyl-3-(5-methyl-4-pyridin-2-yl-1H-imidazol-2-yl)-9H-carbazole;

3-(4,5-dimethyl-1H-imidazol-2-yl)-9-ethyl-9H-carbazole;

9-ethyl-3-(1H-imidazo[4,5-c]pyridin-2-yl)-9H-carbazole;

3-(1H-benzoimidazol-2-yl)-9-ethyl-9H-carbazole;

9-ethyl-3-(3H-imidazo[4,5-b]pyridin-2-yl)-9H-carbazole;

9-ethyl-3-(7H-purin-8-yl)-9H-carbazole; and 2-(9-ethyl-9H-carbazol-3-yl)-1H-benzoimidazole-5-carboxylic acid;

a pharmaceutically acceptable salt thereof or a solvate or hydrate of said compound or said salt.

3. A pharmaceutical composition comprising a compound of claim 1, a pharmaceutically acceptable salt thereof, a prodrug of said compound or said salt, or a solvate or hydrate of said compound, said salt or said prodrug; and a pharmaceutically acceptable excipient, diluent, or carrier.

4. The pharmaceutical composition of claim 3 wherein said compound of claim 1 is selected from the group consisting of 9-ethyl-3-(5-methyl-4-phenyl-1H-imidazol-2-yl)-9H-carbazole; 9-ethyl-3-(4-phenyl-5-trifluoromethyl-1H-imidazol-2-yl )-9H-carbazole; 9-ethyl-3-(5-methyl-4-pyridin-2-yl-1H-imidazol-2-yl)-9H-carbazole; 3-(4,5-dimethyl-1H-imidazol-2-yl)-9-ethyl-9H-carbazole; 9-ethyl-3-(1H-imidazo[4, 5-c]pyridin-2-yl)-9H-carbazole; 3-(1H-benzoimidazol-2-yl)-9-ethyl-9H-carbazole; 9-ethyl-3-(3H-imidazo[4,5-b]pyridin-2-yl)-9H-carbazole; 9-ethyl-3-(7H-purin-8-yl)-9H-carbazole; and 2-(9-ethyl-9H-carbazol-3-yl)-1H-benzoimidazole-5-carboxylic acid; a pharmaceutically acceptable salt thereof or a solvate or hydrate of said compound or said salt.

5. The pharmaceutical composition of claim 3 or 4 further comprising at least one additional pharmaceutical agent.

6. The pharmaceutical composition of claim 5 wherein said at least one additional pharmaceutical agent is selected from the group consisting of an anti-obesity agent, an anorectic agent, a sorbitol dehydrogenase inhibitor, a aldose reductase inhibitor, a glycogen phosphorylase inhibitor, a cholinomimetic agent, an anti-depressant, an antianxiolytic agent, and a typical or atypical antipsychotic agent.

* * * * *